United States Patent [19]

Takano et al.

[11] 4,338,467

[45] Jul. 6, 1982

[54] PROCESS FOR PREPARING ARYLACETALDEHYDES

[75] Inventors: Tetsuo Takano, Takatsuki; Gohu Suzukamo, Ibaraki; Masaru Ishino, Takatsuki; Kiyoshi Ikimi, Kyoto, all of Japan

[73] Assignee: Sumitomo Chemical Company, Limited, Osaka, Japan

[21] Appl. No.: 233,148

[22] Filed: Feb. 10, 1981

[51] Int. Cl.³ .............................................. C07C 45/49
[52] U.S. Cl. .................................................... 568/428
[58] Field of Search ........................................ 568/428

[56] References Cited

U.S. PATENT DOCUMENTS 3,996,288  12/1976  Yukata et al. ...................... 568/428

OTHER PUBLICATIONS

Hung, Chem. Abs., vol. 60 (1964) 2847e.

Primary Examiner—Bernard Helfin
Attorney, Agent, or Firm—Birch, Stewart, Kolasch and Birch

[57] ABSTRACT

A process for preparing an arylacetaldehyde by reacting the corresponding arylmethyl halide with carbon monoxide and hydrogen in the presence of a cobalt compound and a basic reagent in a liquid medium, characterized in that the basic reagent is an alkali metal compound and the liquid medium is a solvent system chosen from nitriles and their mixtures with hydrocarbons, whereby the arylacetaldehyde can be produced in a good yield by the use of a small amount of the cobalt compound as the catalyst.

13 Claims, No Drawings

PROCESS FOR PREPARING ARYLACETALDEHYDES

The present invention relates to a process for preparing arylacetaldehydes from arylmethyl halides by their reaction with carbon monoxide and hydrogen.

Arylacetaldehydes are useful as perfumes and also as intermediates in the production of agricultural chemicals and pharmaceuticals.

For production of arylacetaldehydes by the reaction of arylmethyl halides with carbon monoxide and hydrogen in the presence of a catalyst, there is known a process as disclosed in Hung. P. 150,412 (*Chemical Abstracts*, 60, 2847e, (1964)). This process, however, requires a large quantity of catalyst, and still the yield of the desired compound is poor. Also, Japanese Patent Publication (unexamined) No. 144,503/1978 discloses production of phenylacetaldehyde by reacting benzyl chloride with carbon monoxide and hydrogen in the presence of octacarbonyl dicobalt and an N,N-disubstituted acid amide. However, the yield of the product in this process is at the most about 50% even when the catalyst is used in a large amount.

As the result of an extensive study, it has now been found that the performance of the reaction of arylmethyl halides with carbon monoxide and hydrogen in the presence of a catalyst under the coexistence of an inorganic base as appropriately selected can afford arylacetaldehydes in high yields by the use of a small amount of the catalyst.

According to this invention, there is provided a process for preparing an arylacetaldehyde by reaction of the corresponding arylmethyl halide with carbon monoxide and hydrogen in the presence of a cobalt compound and a basic reagent in a liquid medium, characterized in that the basic reagent is an inorganic alkali metal compound and the liquid medium is a solvent system chosen from nitriles and their mixtures with hydrocarbons.

The arylmethyl halide as the starting material may be any aromatic compound having at least one halomethyl group on the aromatic ring. The aromatic ring may be monocyclic or polycyclic and also condensed or non-condensed. On the aromatic ring, there may be present, in addition to the halomethyl group(s), any other substituent(s) which may be influenced during the reaction but do not inferfere with the reaction on the said halomethyl group(s). Examples of such substituent(s) are $C_1$-$C_6$ alkyl, $C_1$-$C_6$ alkoxy, halogen (e.g. chlorine, bromine, fluorine, iodine), etc. Preferred arylmethyl halides are representable by the formula:

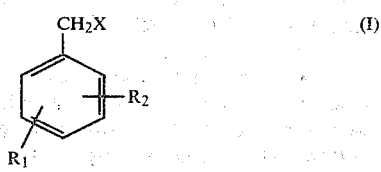

(I)

wherein $R_1$ and $R_2$, which may be same or different, are each hydrogen, $C_1$-$C_6$ alkyl, $C_1$-$C_6$ alkoxy or halogen (particularly chlorine) and X is halogen (particularly chlorine).

Specific examples of the arylmethyl halide (I) are benzyl chloride, p-fluorobenzyl chloride, p-chlorobenzyl chloride, p-methylbenzyl chloride, p-ethylbenzyl chloride, p-isopropylbenzyl chloride, p-tert-butylbenzyl chloride, p-methoxybenzyl chloride, p-ethoxybenzyl chloride, o,p-dimethylbenzyl chloride, etc.

The cobalt compound used as the catalyst may be any one conventionally employed for carbonylation and hydroformylation, which includes complexes having carbon monoxide, phosphines or amines as ligands, carboxylates, halides, hydroxides, oxides, nitrates, etc. Specific examples are cobalt carbonyls, cobalt hydroxide, cobalt carbonate, cobalt acetate, cobalt formate, cobalt naphthenate, cobalt bromide, etc. Among them, particularly preferred are cobalt carbonyls, which include octacarbonyl dicobalt, dodecacarbonyl tetracobalt, hydridotetracarbonyl cobalt, hexacarbonyl bis(tri-n-butylphosphine)dicobalt, etc. In the reaction system in which the basic reagent coexists, these cobalt carbonyls may substantially be converted to cobalt carbonyl anions, for example, the alkali metal salt of tetracarbonyl cobalt which may be catalytically active. A preferred range of the amount of the catalyst is from $10^{-4}$ to $10^{-1}$ gram-atom (calculated as metallic cobalt) based on one mole of the arylmethyl halide.

The inorganic alkali metal compound usable as the basic reagent may be an inorganic compound of alkali metal showing an alkaline property at room temperature (e.g. about 5° to 30° C.) in aqueous solution, and specific examples are oxides, hydroxides, carbonates, phosphates, silicates, borates, etc. Preferred are carbonates of alkali metal, and particularly preferred are sodium carbonate and potassium carbonate. The amount of the inorganic alkali metal compound may be equivalent to or slightly greater than one mole of the arylmethyl halide.

The solvent system, which is preferably used in the process of the invention may be chosen from nitriles and their mixtures with hydrocarbons. Examples of nitriles are acetonitrile, benzonitrile, etc. Examples of hydrocarbons are those having not more than 12 carbon atoms such as cyclohexane. The concentration of the arylmethyl halide in these solvent systems is usually from 1 to 80% by weight, preferably from 5 to 50% by weight.

Carbon monoxide and hydrogen may be introduced into the reaction system separately but they are usually introduced in their mixture form. The molar ratio of carbon monoxide to hydrogen in the mixture is normally 1 or more, preferably from 1 to 5, so that the objective compound will be produced in a high selectivity. The mixture is used normally with a pressure of not less than 10 atm, preferably from 50 to 300 atm. The mixture need not be pure; for example, it may contain an inert gas such as nitrogen or helium.

The reaction temperature is not particularly limited, but a temperature range of 50° to 200° C., preferably of 80° to 160° C., may be employed. The reaction time depends upon the other reaction conditions such as the reaction temperature, but a range of 0.5 to 10 hours is generally adopted.

The reaction may be carried out batchwise and continuously. In order to prevent the reaction system from contamination with metal compounds which may dissolve out of a reactor wall, it is desirable to use a reactor of which the inside wall is protected by glass-lining or anticorrosive materials such as Hastelloy.

The thus produced arylacetaldehyde may be separated from the reaction mixture and purified by per se conventional techniques such as distillation and extraction.

The produced arylacetaldehyde corresponds substantially to the starting arylmethyl halide. The arylacetaldehyde is an aromatic compound having at least one formylmethyl group on the aromatic ring. The aromatic ring may be monocyclic or polycyclic and also condensed or non-condensed. On the aromatic ring, there may be present, in addition to the formylmethyl group(s), any other substituent(s) which are same as or different from those present in the starting arylmethyl halide. Examples of such substituent(s) are $C_1$-$C_6$ alkyl, $C_1$-$C_6$ alkoxy, halogen (e.g. chlorine, bromine, fluorine, iodine), etc. Preferred arylacetaldehydes are representable by the formula:

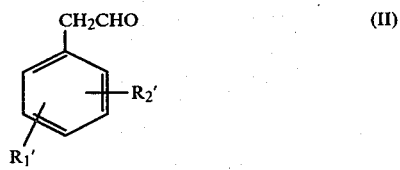 (II)

wherein $R_1'$ and $R_2'$, which may be same or different, are each hydrogen, $C_1$-$C_6$ alkyl, $C_1$-$C_6$ alkoxy or halogen (particularly chlorine).

Specific examples of the arylacetaldehyde (II) are phenylacetaldehyde, p-fluorophenylacetaldehyde, p-chlorophenylacetaldehyde, p-methylphenylacetaldehyde, p-ethylphenylacetaldehyde, p-isopropylphenylacetaldehyde, p-tertbutylphenylacetaldehyde, p-methoxphenylacetaldehyde, p-ethoxyphenylacetaldehyde, o,p-dimethylphenylacetaldehyde, etc.

The process of this invention will be illustrated specifically with reference to the following examples, which are not however to be interpreted as limiting the invention thereto.

Identification and determination of the product were made by IR spectrum, NMR spectrum and gas chromatography. The conversion, selectivity and yield of the product are based on the following equations:

$$\text{Conversion} = \frac{\text{Moles of arylmethyl halide consumed}}{\text{Moles of arylmethyl halide used}} \times 100\ (\%)$$

$$\text{Selectivity} = \frac{\text{Moles of arylacetaldehyde produced}}{\text{Moles of arylmethyl halide consumed}} \times 100\ (\%)$$

$$\text{Yield} = \frac{\text{Moles of arylacetaldehyde produced}}{\text{Moles of arylmethyl halide used}} \times 100\ (\%)$$

EXAMPLE 1

Into a 50 ml SUS autoclave, there were charged p-methylbenzyl chloride (0.70 g), octacarbonyl dicobalt (0.068 g), sodium carbonate (0.60 g) and acetonitrile (10 ml). After replacing air in the autoclave by nitrogen, a mixed gas comprising carbon monoxide and hydrogen in a molar ratio of 1:4 was introduced therein to make a pressure of 100 atm. The contents of the autoclave were heated at 100° C. for 5 hours with stirring, cooled to room temperature and analyzed by gas chromatography to obtain the following results: conversion of p-methylbenzyl chloride, 100%; yield of p-methylphenylacetaldehyde, 91.0%.

REFERENCE EXAMPLE 1

In the same manner as in Example 1 but using methylethylketone (10 ml) in place of acetonitrile, the reaction was carried out. The results were as follows: conversion of p-methylbenzyl chloride, 73.6%; yield of P-methylphenylacetaldehyde, 43.7%.

EXAMPLE 2

Into the same autoclave as in Example 1, there were charged p-methylbenzyl chloride (1.40 g), octacarbonyl dicobalt (0.034 g), sodium carbonate (1.10 g), cyclohexane (10 ml) and acetonitrile (1 ml). After replacing air in the autoclave by nitrogen, a mixed gas comprising carbon monoxide and hydrogen in a molar ratio of 1:4 was introduced therein to make a pressure of 100 atm. The contents of the autoclave were heated at 100° C. for 3 hours with stirring, cooled to room temperature and analyzed by gas chromatography to obtain the following results: conversion of p-methylbenzyl chloride, 99.7%; yield of p-methylphenylacetaldehyde, 90.1%. p-Xylene was by-produced in an amount of 8.8 mole % based on p-methylbenzyl chloride used.

EXAMPLES 3 to 4 AND REFERENCE EXAMPLE 2

In the same manner as in Example 1 but using benzyl chloride (0.63 g) and various kinds of inorganic bases, the reaction was carried out. The results were as shown in Table 1.

TABLE 1

| Example No. | Inorganic base | Conversion of benzyl chloride (%) | Phenylacetaldehyde Yield (%) | Phenylacetaldehyde Selectivity (%) |
|---|---|---|---|---|
| 3 | Sodium carbonate (0.60 g) | 86.6 | 76.5 | 88.3 |
| 4 | Potassium carbonate (0.70 g) | 81.5 | 70.5 | 86.5 |
| Reference 2 | Sodium acetate (0.82 g) | 17.8 | 12.4 | 69.6 |

EXAMPLE 5

In the same manner as in Example 1 but using benzyl bromide (0.90 g) and adopting a reaction time of 2 hours, the reaction was carried out. The results were as follows: conversion of benzyl bromide, 92.7%; selectivity to phenylacetaldehyde, 73.7%; yield of phenylacetaldehyde, 68.3%.

EXAMPLE 6

In the same manner as in Example 1 but using o-chlorobenzyl chloride (0.81 g), the reaction was carried out. The results were as follows: conversion of o-chlorobenzyl chloride, 90.6%; selectivity to o-chlorophenylacetaldehyde, 74.5%; yield of o-chlorophenylacetaldehyde, 67.5%.

What is claimed is:

1. A process for preparing an arylacetaldehyde by reacting the corresponding arylmethyl halide with carbon monoxide and hydrogen in the presence of a cobalt compound and a basic reagent in a liquid medium, and wherein:
   a. said basic reagent is an alkali metal compound;
   b. said liquid medium is a solvent system selected from the group consisting of nitriles and nitriles mixed with hydrocarbons;
   c. said arylmethyl halide is a monocyclic or polycyclic, condensed or non-condensed aromatic compound having at least one halomethyl group on the aromatic ring which may be substituted with one or more substituents selected from the group consisting of $C_1$–$C_6$ alkyl, $C_1$–$C_6$ alkoxy and halogen;
d. said cobalt compound is elected from the group consisting of carboxylates, hydroxides, halides, oxides and nitrates of cobalt and cobalt complexes of carbon monoxide, having phosphine or amine as a ligand;
e. said alkali metal compound is an oxide, hydroxide, carbonate, phosphate, silicate or borate of an alkali metal;
f. said reaction is carried out under a pressure of 10 atm or more; and
g. said reaction is carried out at a temperature range of from 50° to 200° C.

2. The process according to claim 1, wherein the arylmethyl halide is a compound of the formula:

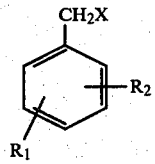

wherein $R_1$ and $R_2$, which may be same or different, are each hydrogen, $C_1$–$C_6$ alkyl, $C_1$–$C_6$ alkoxy or halogen and X is halogen.

3. The process according to claim 1, wherein the arylmethyl halide is benzyl chloride, p-fluorobenzyl chloride, p-chlorobenzyl chloride, p-methylbenzyl chloride, p-ethylbenzyl chloride, p-isopropylbenzyl chloride, p-tert-butylbenzyl chloride, p-methoxybenzyl chloride, p-ethoxybenzyl chloride or o,p-dimethylbenzyl chloride.

4. The process according to claim 1, wherein the cobalt compound is octacarbonyl dicobalt, dodecacarbonyl tetracobalt, hydridotetracarbonyl cobalt or hexacarbonyl bis(tri-n-butylphosphine)dicobalt.

5. The process according to claim 1, wherein the amount of the cobalt compound added is from $10^{-4}$ to $10^{-1}$ gram-atom (calculated as metallic cobalt) based on one mole of the arylmethyl halide.

6. The process according to claim 1, wherein the inorganic alkali metal compound is the carbonate of an alkali metal.

7. The process according to claim 6, wherein the carbonate of an alkali metal is sodium carbonate or potassium carbonate.

8. The process according to claim 1, wherein the amount of the inorganic alkali metal compound is equivalent to or slightly greater than one mole of the arylmethyl halide.

9. The process according to claim 1, wherein the solvent system is a nitrile or a mixture of a nitrile with a hydrocarbon.

10. The process according to claim 9, wherein the hydrocarbon contains not more than 12 carbon atoms.

11. The process according to claim 9, wherein the concentration of the arylmethyl halide in the solvent system is from 1 to 80% by weight.

12. The process according to claim 1, wherein the molar ratio of carbon monoxide to hydrogen is kept at 1 or more.

13. The process according to claim 1, wherein the reaction is carried out for a period of 0.5 to 10 hours.

* * * * *